United States Patent [19]

Hill

[11] Patent Number: 4,620,318
[45] Date of Patent: Oct. 28, 1986

[54] FOVEA-CENTERED EYE FUNDUS SCANNER

[75] Inventor: Robert B. Hill, Portland, Oreg.

[73] Assignee: EYE-D Development II Ltd., Portland, Oreg.

[21] Appl. No.: 486,014

[22] Filed: Apr. 18, 1983

[51] Int. Cl.⁴ .......................... G06K 9/00; A61B 3/10
[52] U.S. Cl. ........................................ 382/2; 350/6.5; 351/200; 351/208; 351/221; 354/62; 382/65
[58] Field of Search .................. 382/2, 65, 5; 350/6.2, 350/6.3, 6.4, 6.5, 6.9, 6.91; 351/200, 206, 208, 211, 221; 354/62

[56] References Cited

U.S. PATENT DOCUMENTS

| | | | |
|---|---|---|---|
| 2,940,371 | 6/1960 | Thurow | 354/62 |
| 3,611,290 | 10/1971 | Luisi et al. | 382/5 |
| 3,762,803 | 10/1973 | Papritz | 351/7 |
| 3,869,694 | 3/1975 | Merchant et al. | 351/7 |
| 3,936,844 | 2/1976 | Matsumara | 354/62 |
| 4,026,638 | 5/1977 | Govignon | 351/7 |
| 4,034,401 | 7/1977 | Mann | 351/7 |
| 4,068,932 | 1/1978 | Ohta et al. | 351/9 |
| 4,109,237 | 8/1978 | Hill | 382/2 |
| 4,166,695 | 9/1979 | Hill et al. | 351/211 |
| 4,169,663 | 10/1979 | Murr | 351/7 |
| 4,213,678 | 7/1980 | Pomerantzeff et al. | 351/7 |
| 4,253,743 | 3/1981 | Matsumura | 354/62 |
| 4,266,861 | 5/1981 | Sawa | 351/7 |
| 4,279,478 | 7/1981 | Matsumura | 354/62 |
| 4,287,410 | 9/1981 | Crane et al. | 351/7 |
| 4,304,483 | 12/1981 | Whitten | 354/62 |
| 4,393,366 | 7/1983 | Hill | 382/2 |

Primary Examiner—Leo H. Boudreau
Assistant Examiner—Joseph Mancuso
Attorney, Agent, or Firm—Eugene D. Farley

[57] ABSTRACT

An apparatus and method for identifying individuals through the ocular reflectance pattern from the fundus of the eye. A fixation target is provided for positioning and focusing the eye of an individual along its visual axis, being centered on the fovea of the eye. An infrared source provides a substantially collimated source beam of infrared radiation. A scanner directs the infrared radiation into the fixated eye from a plurality of sequential angularly divergent positions forming a substantially circular locus of points substantially centered on the fovea. The light is reflected in part out of the eye and forms a reflected beam. A detector measures the intensity of the radiation reflected from the eye at each sequential location, the intensities being recorded as an identification pattern. At a later date the eye may be presented again to the apparatus in a different rotational position about its visual axis and another pattern generated. The two patterns will be substantially the same, varying only in the relative start points of the data sequences. One pattern may be rotated with respect to the other pattern to ascertain that the two patterns match, thus verifying the identity of the individual.

7 Claims, 3 Drawing Figures

FOVEA-CENTERED EYE FUNDUS SCANNER

BACKGROUND OF THE INVENTION

This invention relates to apparatus and method for recognizing an individual and/or for verifying an individual's identity. It pertains particularly to an apparatus for obtaining an identification pattern from the ocular reflection from the fundus of the eye of an individual, irrespective of head-tilt.

My previous patent, U.S. Pat. No. 4,109,237 discloses a basic method and apparatus for identifying individuals through their retinal vasculature patterns. My subsequent patent, U.S. Pat. No. 4,393,366, discloses using a rotating beam scanner for obtaining the identification pattern from the fundus of an eye.

Previously, it was believed that the identification pattern, carrying sufficient information, could be obtained best by centering on the optic nerve. In that way the blood vessels emerging from the optic nerve and forming the retinal vasculature could be used for obtaining the individual identification pattern. However, it has been found that by the use of infrared radiation the vasculature of the choroid becomes readily and accurately detectable. The choroidal vasculature forms a matting behind the retina even in the area of the macula and fovea, where retinal blood vessels are very small or non-existent. The blood vessels of the choroid are stable, as are those of the retina, and thus may be used for obtaining information as to an individual's identity.

The eye naturally fixates and centers images on the fovea. When fixating on any target the eye comes to a position with its visual line passing through the center of the eye and intersecting the fovea. However, the optic nerve enters the eye off axis, approximately 15.5 degrees toward the nasal side of the eye. In my previous patents an off-axis scanner was disclosed which caused a scan to be taken around the optic nerve while the eye was fixated on the fovea.

However, it has been found that a problem at times is encountered in obtaining consistent identification patterns with a given subject. The problem is caused by rotation of the eye about its visual line when the subject tilts his head. In the off-axis scanner a different part of the eye will be scanned if the head is tilted. It is true that as the head tilts the eye has a tendency to right itself to a level position. However, this tendency is not sufficiently accurate to compensate entirely for head tilt. Accordingly, it is necessary for the subject to locate his head in almost exactly the same rotational position each time a scan is made.

The present invention overcomes this difficulty.

It is the general object of this invention to provide an improved apparatus and method for obtaining and recording an identification pattern from the reflection of light from the fundus of an eye.

It is another object to provide such an apparatus which takes a circular scan centered on the eye fovea.

It is another object to provide an infrared light source which will detect the vasculature of the choroid and which will not affect pupil dilation during the pattern-recording scan.

It is yet another object to provide a fixation apparatus which will repeatably position the eye and orient it along its visual line.

It is a further object to provide a fixation means which is operable to cause the pupil to dilate or constrict.

It is another object to provide correct optical refraction or focus for each user.

It is a still further object to pass the fixation, source and reflected beams through common optical elements on a common visual axis, thereby reducing the complexity and cost of the apparatus.

These and other objects and advantages of the present invention and the manner in which they are achieved will be made apparent in the following specification and claims.

SUMMARY OF THE INVENTION

In its basic concept the present invention is an apparatus and method for identifying individuals through the ocular light reflection pattern from the fundus of the eye. The device provides a fixation beam along the visual line of the eye, and a scanner for obtaining an identification pattern in a substantially circular pattern centered around the fovea. The apparatus makes use of infrared light in order to observe the vasculature of the choroid as well as the vasculature of the retina.

DESCRIPTION OF THE PREFERRED EMBODIMENT

In the present invention a circular scan centered on the fovea, and therefore about the visual axis, is used such that eye rotation about the visual axis will not result in the generation of substantially different patterns from a given individual when the individual tilts his head. This is because the area scanned on the fundus varies only in rotation; the sequence of the data remains the same.

The identification process involves two basic steps. The first is an enrollment wherein the individual learns how to use the device and a reference pattern is acquired and stored.

In the second step an individual's identity is either verified or recognized automatically with the device. Recognition implies automatic selection of the correct reference pattern for identification. Verification implies a comparison to a pre-selected reference pattern.

Figure 3:
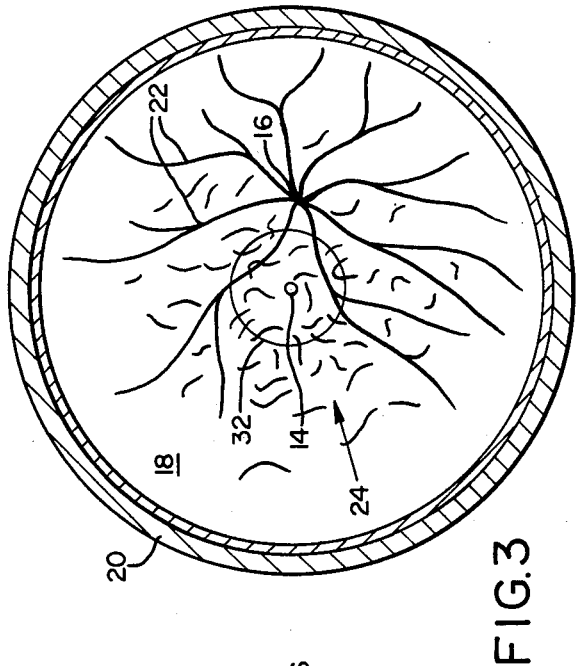
FIG. 3 is a section taken along the line 3—3 of FIG. 2 illustrating the fundus of the eye.
Figure 2:
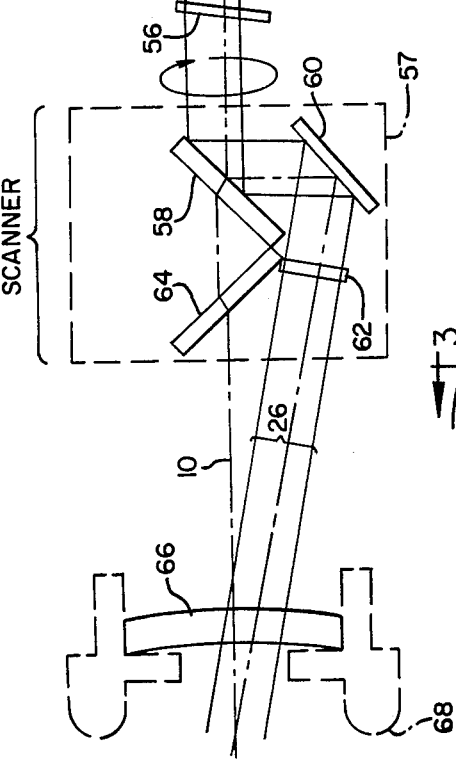
FIG. 2 is a diagrammatic top sectional view of an eye showing the refraction of rays entering therein.

FIGS. 2 and 3 illustrate an eye into which the scanner beam is projected. The eye is centered on visual line or axis 10 which intersects fundus 12 at the fovea 14. Optic nerve 16 is approximately 15.5 degrees off the visual line.

Fundus 12 includes the retina 18 and the choroid 20. As shown in FIG. 3, the retinal vasculature 22 branches from the area of optic nerve 16. The retinal vasculature is readily apparent on observation with either visible or infrared light. With infrared radiation the vasculature of the choroid also becomes observable and is denoted by the matting of the choroidal vessels 24. These choroidal vessels are apparent even in the area of the fovea. Thus the scan picks up a combination of the retinal vasculature, choroidal vasculature and various other structures and pigmentation.

As will be hereinafter described in detail, the scanner produces a substantially collimated source beam 26 which enters the pupil 28 of the eye and is refracted by lens 30 to substantially focus on fundus 12. The scan forms a circular locus of points 32 substantially centered on fovea 14.

Figure 1:
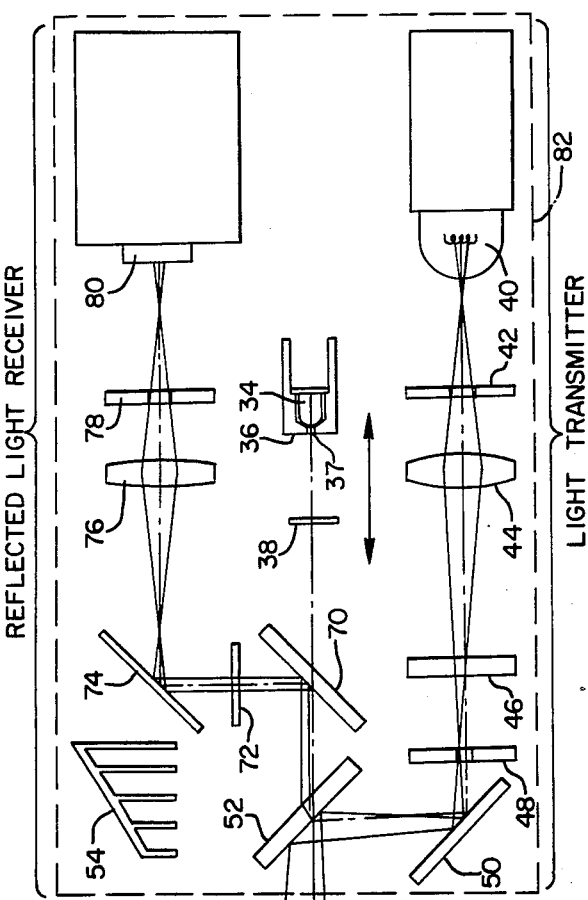
FIG. 1 is a schematic plan view of the optics of the apparatus of the present invention.

Now turning to FIG. 1, the apparatus of the present invention includes a fixation means providing a fixation beam for positioning and focusing the eye of an individual along its visual axis. This includes a visible light source, preferably a diffuse light-emitting diode 34, in a mounting 36 having a pin hole 37. The light-emitting diode illuminates a fixation reticle 38 which is preferably a plate with multiple concentric circles or other targeting patterns thereon. This provides a target onto which the eye is focused. The remainder of the path of the fixation beam is directed through elements also common to the source and receiver optics.

Infrared source means is provided to create a beam of infrared light or radiation to be directed into the subject's eye. Preferably this includes an incandescent tungsten bulb 40 which produces light, part of which is in the infrared spectrum, having a wave length of preferably, from about 0.7 to about 0.95 microns. The light passes through a spatial filter 42 and is refracted by a lens 44. An infrared filter 46 passes only the infrared portion of the beam. The beam passes through another pinhole or spatial filter 48. The beam is then reflected by a mirror 50 onto a beam splitter 52 which is coincident with the fixation optics and the visual line.

Part of the source radiation is transmitted through the beam splitter and is lost in a light trap 54. The remainder of the beam is reflected along the visual line into an objective lens 56. The objective lens is preferably tilted at a small angle, e.g. about 6°, to reduce reflections. The objective lens substantially collimates the beam and directs it along the visual axis.

A scanner means is provided for directing the beam into the fixated eye from a plurality of sequential, angularly divergent positions. Preferably the scanner means includes a rotatable housing 57 and optics which rotate with the housing, as indicated by the circular arrow of FIG. 1.

A hot mirror 58, which is a mirror which reflects infrared light while passing visible light, is located in the path of the source beam and the fixation beam. The fixation beam of visible light is substantially passed through the hot mirror, while the source beam of infrared light is substantially reflected off axis. A scanner mirror 60 is mounted in the housing at a point spaced from the axis and is oriented to direct the beam into the eye as the housing rotates. The beam is directed to an apex at the pupil of the eye.

Also mounted in the scanner is an infrared filter 62 which eliminates any visible light which may have been reflected from the fixation beam by hot mirror 58.

Hot mirror 58 causes a slight off axis displacement of the fixation beam and an offset plate 64 is provided to null the displacement of the fixation beam.

An objective lens 66 is mounted in an eyepiece 68 and substantially collimates the beam and directs it into the eye. The objective lens at this location serves to provide easier focusing of the device for those individuals who do not have exactly 20—20 vision, as will be subsequently discussed.

As housing 57 rotates, the beam directed into the eye forms a circular scan, or locus of points, substantially centered on the fovea. The scan circle may be of any size selected, and is represented by the circle shown in FIG. 3 at 32.

The light reflected out of the eye varies in intensity depending on the structures encountered in the scan. Reflected light is re-collimated by the lens of the eye 30 and directed out of the pupil in a reverse direction. The reflected beam passes back through objective lens 66 and filter 62 and reflects off of scanner mirror 60 and hot mirror 58. It is then focused by objective lens 56. Beam splitter 52 passes a portion of the reflected scanning beam. A hot mirror 70 reflects this portion of the reflected beam to the receiver.

The reflected beam passes through a spatial filter 72 and is reflected by a mirror 74. The beam then is refracted by a lens 76 and passed through another spatial filter 78 to a detector 80.

A carriage 82 mounts the fixation, source and receiver optics, and movement of the carriage in the longitudinal direction serves to vary the focus for individuals who do not have 20—20 vision. All of the beams focus at optically equal distances from the eye and exit the carriage coincidentally. Therefore when the user focuses on the fixation target he also focuses the source and receiver optics. Both objective lens 56 and objective lens 66 serve to substantially collimate the final beam when the user has 20—20 vision. Moving the carriage varies the beam from a true column but this discrepancy is compensated for by the lens 30 of the user's eye. The objective lens at the position of lens 66 allows the carriage to compensate for focusing changes by moving a shorter distance.

The fixation mounting 36 with its pinhole 37 preferably is secured to the carriage in such a manner that it can be spatially adjusted a minute amount. This adjustment allows fine tuning of the fixation axis to coincide with the scanner axis as set forth in my copending patent application Ser. No. 235,150.

The light from the fixation light-emitting diode 34 is preferably variable in intensity to vary the pupil size of the individual. The size of the subject's pupil will vary, depending on the intensity of the visible light from the fixation target, but will not be affected by the infrared radiation.

OPERATION

The individual to be identified must first enroll himself in the data base of qualified users of the system. In the enrollment process an initial scan pattern is recorded.

The individual presents his eye to the apparatus by moving his head adjacent eyepiece 68 and peering into lens 66. The fixation reticle 38 is visible and the user fixates his eye on this target. If the reticle appears out of focus, the focus may be adjusted by moving carriage 82.

With the eye centered on the visual line and in the appropriate longitudinal position, the individual then initiates the scan sequence. Scanner 57 rotates, and when it is up to speed the infrared source bulb 40 is turned on. The source beam is directed into the eye from a plurality of sequential angularly divergent positions as the scanner rotates. The beam impinges on the fundus and sequentially forms a circular locus of points substantially centered on the fovea. A portion of the light is reflected from the fundus forming a reflected beam. The intensity of the reflected beam is determined by the vasculature pattern and measured by detector 80 at each sequential point. The amounts of light thus sensed form the identification pattern.

When it is desired to verify or recognize the identity of the individual, he again places his eye in the appropriate position and repeats the scan. The pattern obtained the second time should be substantially the same as the reference pattern. Comparison may be done by any means but is preferably accomplished by high speed digital computers, in the manner described in detail in my aforesaid U.S. Pat. No. 4,,109,237 and U.S. patent application, Ser. No. 235,150, now U.S. Pat. No. 4,393,366.

Should the eye be presented to the apparatus in such an orientation that it is rotated about the visual line, the pattern then obtained will be rotated with respect to the reference pattern. However, the sequence of the data remains the same. The two patterns are compared while rotating one pattern with respect to the other pattern until it is noted that the two patterns match. Such a comparison can be done very quickly by a computer.

It is important to note that the foregoing comparison can be accomplished because the scan is substantially circular and is centered on the fovea. Inconsistencies resulting from subject head tilt accordingly are eliminated.

Having described my invention in its preferred embodiment, I claim:

1. Apparatus for identifying individuals through the ocular light reflection pattern from the fundus of the eye, comprising:
    (a) fixation means providing a fixation beam of visible light for positioning and focusing the eye of an individual along its visual axis, said axis being centered on the fovea,
    (b) source means providing a source beam of infrared radiation,
    (c) scanner means positioned for receiving the source beam and for directing it into the fixated eye from a plurality of sequential angularly divergent positions, in order to form a substantially circular locus of points substantially centered on the fovea, the source beam being directed along the visual axis into the scanner means, the scanner means comprising a housing rotatable about the visual axis, a first mirror mounted in the housing for reflecting the source beam of axis, and a second mirror mounted in the housing at a point spaced from the axis and oriented to direct the source beam into the eye as the housing rotates, and
    (d) receiver means positioned for detecting the intensity of the light radiation reflected from the eye at each sequential location.

2. The apparatus of claim 1 wherein the fixation beam and the source beam enter the scanner means coincidentally, and wherein the first mirror comprises a hot mirror which selectively substantially passes the visible light of the fixation beam and substantially reflects the infrared radiation of the source beam.

3. The apparatus of claim 2 further comprising an offset plate mounted in the housing of the scanner means, through which the fixation beam passes, the offset plate being mounted at an angle to substantially null displacement of the fixation beam introduced by passing through the hot mirror.

4. The apparatus of claim 2 further comprising an infrared filter mounted in the housing through which the source beam passes after being reflected off the hot mirror, the infrared filter blocking any visible light in the source beam.

5. The apparatus of claim 1 wherein the fixation means, source means and receiver means are at substantially optically equal distances from the eye, and including movable carriage means for mounting said fixation means, source means and receiver means, thereby enabling varying the focus of the beams at the eye.

6. The apparatus of claim 1 wherein the fixation means comprises variable brightness fixation means for varying the pupil size of the individual.

7. The apparatus of claim 1 wherein the fixation means comprises spatially-adjustable fixation means to fine tune the alignment of the apparatus.

* * * * *